United States Patent
Dolgos et al.

(10) Patent No.: US 9,293,110 B2
(45) Date of Patent: Mar. 22, 2016

(54) BATCH PARAMETER SETTINGS IN A MEDICAL APPARATUS

(71) Applicant: B. Braun Avitum AG, Melsungen (DE)

(72) Inventors: Sandor Dolgos, Szentendre (HU); Robert G. Schin, Budapest (HU); Peter Szamko, God (HU); Gabor Kinoranyi, Budapest (HU)

(73) Assignee: B. BRAUN AVITUM AG, Melsungen (DE)

( * ) Notice: Subject to any disclaimer, the term of this patent is extended or adjusted under 35 U.S.C. 154(b) by 85 days.

(21) Appl. No.: 13/872,434

(22) Filed: Apr. 29, 2013

(65) Prior Publication Data

US 2013/0293570 A1 Nov. 7, 2013

(30) Foreign Application Priority Data

May 3, 2012 (EP) .................................... 12166671

(51) Int. Cl.
*G09G 5/00* (2006.01)
*A61M 1/16* (2006.01)
*G06F 19/00* (2011.01)

(52) U.S. Cl.
CPC ................ *G09G 5/003* (2013.01); *A61M 1/16* (2013.01); *G06F 19/3406* (2013.01); *A61M 2205/18* (2013.01); *A61M 2205/505* (2013.01); *A61M 2205/70* (2013.01)

(58) Field of Classification Search
CPC ..................................................... G09G 5/003
USPC ........................................................ 345/619
See application file for complete search history.

(56) References Cited

U.S. PATENT DOCUMENTS

| 8,001,967 | B2 | 8/2011 | Wallace et al. |
| 2005/0256444 | A1* | 11/2005 | O'Mahony et al. .......... 604/5.02 |
| 2007/0158268 | A1 | 7/2007 | DeComo |
| 2008/0256489 | A1* | 10/2008 | Maurer et al. ................. 715/833 |
| 2011/0017667 | A1 | 1/2011 | Delmage et al. |
| 2011/0029865 | A1* | 2/2011 | Gilland et al. ................. 715/702 |
| 2011/0224523 | A1* | 9/2011 | Budiman ........... A61B 5/14532 600/365 |

FOREIGN PATENT DOCUMENTS

DE 100 13 666 10/2001

OTHER PUBLICATIONS

European Search Report for EP 12166671 dated Oct. 9, 2012.

* cited by examiner

*Primary Examiner* — Mark Zimmerman
*Assistant Examiner* — Vu Nguyen
(74) *Attorney, Agent, or Firm* — RatnerPrestia

(57) ABSTRACT

Methods for setting mutually dependent parameters of a microprocessor controlled medical apparatus are disclosed. Mutually dependent parameters may be set by displaying mutually dependent parameter settings, displaying possible values for at least one parameter setting, whereby limits of the range of possible values is mutable and is automatically determined based on the current parameter settings, adjusting a parameter setting upon manual selection by an operator, automatically determining and displaying the value of at least one parameter setting depending on the parameter setting that is adjusted by the operator, whereby the determination of the dependent parameter setting is based on a stored relationship between parameter settings, implementing the set of adjusted parameter settings by actuating a batch setting acceptance operation, and operating the medical apparatus based on the set of adjusted parameter settings.

17 Claims, 3 Drawing Sheets

BATCH PARAMETER SETTINGS IN A MEDICAL APPARATUS

CROSS REFERENCE TO RELATED APPLICATIONS

This application claims priority to European Application No. EP 12 166 671.3 filed May 3, 2012, the contents of such application being incorporated by reference herein.

FIELD OF THE INVENTION

The invention relates to a method for setting mutually dependent parameters of a microprocessor controlled medical apparatus that comprises at least a software component driving a user interface connected to a screen.

The invention further relates to a medical apparatus using this method.

BACKGROUND OF THE INVENTION

Modern medical apparatuses are often controlled by a microprocessor that, for example, operates pumps, reads sensors and communicates with an operator via a user interface like a monitor, keypad and/or touchscreen. This user interface can make use of text, pictograms and/or graphical icons to guide an operator through the setup and give him/her necessary information during a therapy that is performed by the medical apparatus. Thereby, parameter input is an essential part of such medical equipment.

For example, extracorporeal blood treatment (ECB) involves the continuous withdrawal of blood from a patient, where the blood is processed within a medical device outside of the patient and is then returned to the patient. Thereby, parameters like the ultrafiltration volume, the therapy time and the ultrafiltration rate can be input by a nurse depending on the patient' prescription, and the medical apparatus can then individually perform the therapy for each patient. The traditional way is the separate input of parameters, i.e. one by one entering the values by any means. However, some of such parameters are mutually dependent from each other and possibly from even the time passed during the therapy, which can cause usability problems.

The main disadvantage of this traditional way of parameter entering is the frequent need of several iterative inputs of such dependent parameters, which basically means a poor usability. First of all, it wastes time to enter and confirm the later possibly improper parameter value. Furthermore, the explanatory power why a desired value of a parameter cannot be entered or what value is possible to be entered is poor.

DESCRIPTION OF THE RELATED ART

Therefore, US 2005/0256444 A1, for example, suggests a user interface for a blood treatment device which allows to select and review a series of parameter settings and to implement the settings in batch manner. Thereby, the graphical user interface (GUI) automatically adjusts dependent settings like the filtration rate as the user adjusts primary settings like the blood flow rate. The effect of each setting change on another setting may be viewed in real time before they are actively enabled. Furthermore, limits for settings are established and if a value that is input by an operator falls below or above a limit, an alarm is issued. The alarm comes along with a message explaining the reasons for the alarm, and the user then has to reconsider his/her input before amended parameters are confirmed and implemented to control the processes of the extracorporeal blood treatment device.

SUMMARY OF THE INVENTION

Based on the prior art it is an objective of the invention to provide a method for setting mutually dependent parameters of a microprocessor controlled medical apparatus with improved usability. It is another objective of the invention to provide a corresponding medical apparatus.

According to aspects of the invention, this objective is achieved by a method having the features of independent Claim 1. Advantageous refinements of this method are set forth in dependent Claims 2 through 14. The objective is also achieved by a medical apparatus according to Claim 15.

Accordingly, a method for setting mutually dependent parameters of a microprocessor controlled medical apparatus is provided, said medical apparatus comprising a user interface for setting said parameters, a screen for displaying said parameters and a storage unit in which a set of rules is stored defining relationships between mutually dependent parameters, wherein upon change of a first parameter, range limits of at least one second parameter are set as a function of rules defining relationships between said first parameter and said at least one second parameter Alternatively, the method according to aspects of the invention can be used for setting mutually dependent parameters of a microprocessor controlled medical apparatus, whereby processes of the medical apparatus are operated based on these parameter settings. The medical apparatus therefore comprises means for manual selection and amendment of the parameter settings by an operator, and the method comprises at least the following steps:

displaying on the screen a set of at least two mutually dependent parameter settings;

displaying on the screen a range of possible values for at least one parameter setting, whereby at least one of the limiters of the range of possible values is mutable and is automatically determined based on the current parameter settings;

adjusting a parameter setting upon manual selection by an operator;

automatically determining and displaying the value of at least one parameter setting depending on the parameter setting that is adjusted by the operator, whereby the determination of said dependent parameter setting is at least based on the stored relationships between parameter settings;

implementing the set of amended parameter settings by actuating a batch setting acceptance operation; and operating the processes of the medical apparatus based on the set of amended parameter settings.

The invention involves a new way of handling parameters which comprises validating and confirming the mutually dependent parameters together (in a batch) and not one by one. Furthermore, it is displayed how the change of one parameter affects the others right away at the change, whereby the possible parameter ranges at the change of any of the parameters are displayed, too, and they can be considered by the operator before parameters are set and implemented to operate the processes of the medical apparatus.

Since adjusting a parameter in the input window should obviously and visibly be avoided beyond the allowable ranges of low and high limits, there is no need for explanatory messages why a parameter value had to be refused. Thus, support and advice regarding the allowable input of a parameter is indirectly done by controlling a derived parameter within its allowable range.

Thereby, at least one of the limiters of a range of possible values is mutable and can automatically be adjusted based on different information. Thus, the range of possible values for at least one dependent parameter setting is automatically determined and displayed when a parameter setting is adjusted by the operator, whereby the determination of said dependent range is at least based on the stored relationships between parameter settings.

In one embodiment of the invention, the parameter settings cannot be adjusted to values beyond the respective ranges of possible values in order to prevent inappropriate or even dangerous parameter settings. However, if the parameter settings can be adjusted to values beyond the respective ranges of possible values, said adjustment can be indicated visually and/or acoustically. Hereby, the operator is informed of this condition of operation.

The determination of dependent parameter settings and/or ranges of possible values for parameter settings can further be based on additional data that is provided to the software component. For example, data input by the operator and/or data stored in the storage unit can be used for such determination. Furthermore, the determination of dependent parameter settings can be based on priority rules that are stored in the storage unit. For example, if the absolute value of a parameter is considered more important than the limit of another parameter, said less important limit may be amended automatically.

In one embodiment of the invention, the medical apparatus is an extracorporeal blood treatment device, and the parameter settings comprise at least the ultrafiltration volume, the therapy time and/or the ultrafiltration rate. Alternatively or in addition, parameters like the blood flow can be set, for example, whereby the operator can preferably choose the selection of possible parameter settings.

Preferably, at least one range of possible values for a parameter setting is automatically adjusted as a function of the therapy time. Consequently, a parameter can reach a limiter of its range of possible values during therapy without any changes of the respective parameter by the operator. In that case, this parameter setting can automatically be adjusted to possible values, when a mutable limiter of the time dependent range of possible values becomes equal to a current parameter setting. Alternatively or in addition, it is indicated visually and/or acoustically, when a mutable limiter of the time dependent range of possible values becomes equal to a current parameter setting. Hereby, the operator is informed of this condition of operation.

The parameter settings as well as the ranges of possible values can be displayed on the screen in many different ways. In one embodiment of the invention, they are displayed in numerical form. In another embodiment, they are displayed by means of sliders on a labeled scale, and combinations of these embodiments are possible, too.

Preferably, the screen is a touchscreen, and the batch setting acceptance operation for implementing a set of amended parameter settings is actuated by a soft button on the touchscreen. Alternatively or in addition, the medical apparatus can comprise a hardware button that can be used by the operator to actuate the batch setting acceptance operation for implementing a set of amended parameter settings.

The invention further comprises a medical apparatus, comprising at least a software component driving a user interface connected to a screen and a storage unit in which a set of rules is stored that defines the relationship between mutually dependent parameter settings based on which the medical apparatus is operated. The medical apparatus further comprises means for manual selection and amendment of the parameter settings by an operator and means for setting and implementing mutually dependent parameters with the described method.

Preferably, the method according to aspects of the invention can be used in an extracorporeal blood treatment device that performs hemodialysis, hemofiltration, hemodialfiltration, ultrafiltration and/or plasmapheresis, for example, but the invention is not limited to this application. Since parameter set up can be important for all kinds of medical apparatuses, the invention can have advantages for other applications, too.

Additional advantages, special features and practical refinements of the invention can be gleaned from the dependent claims and from the presentation below of preferred embodiments making reference to the figures.

DETAILED DESCRIPTION OF THE PREFERRED EMBODIMENTS

Figure 1:
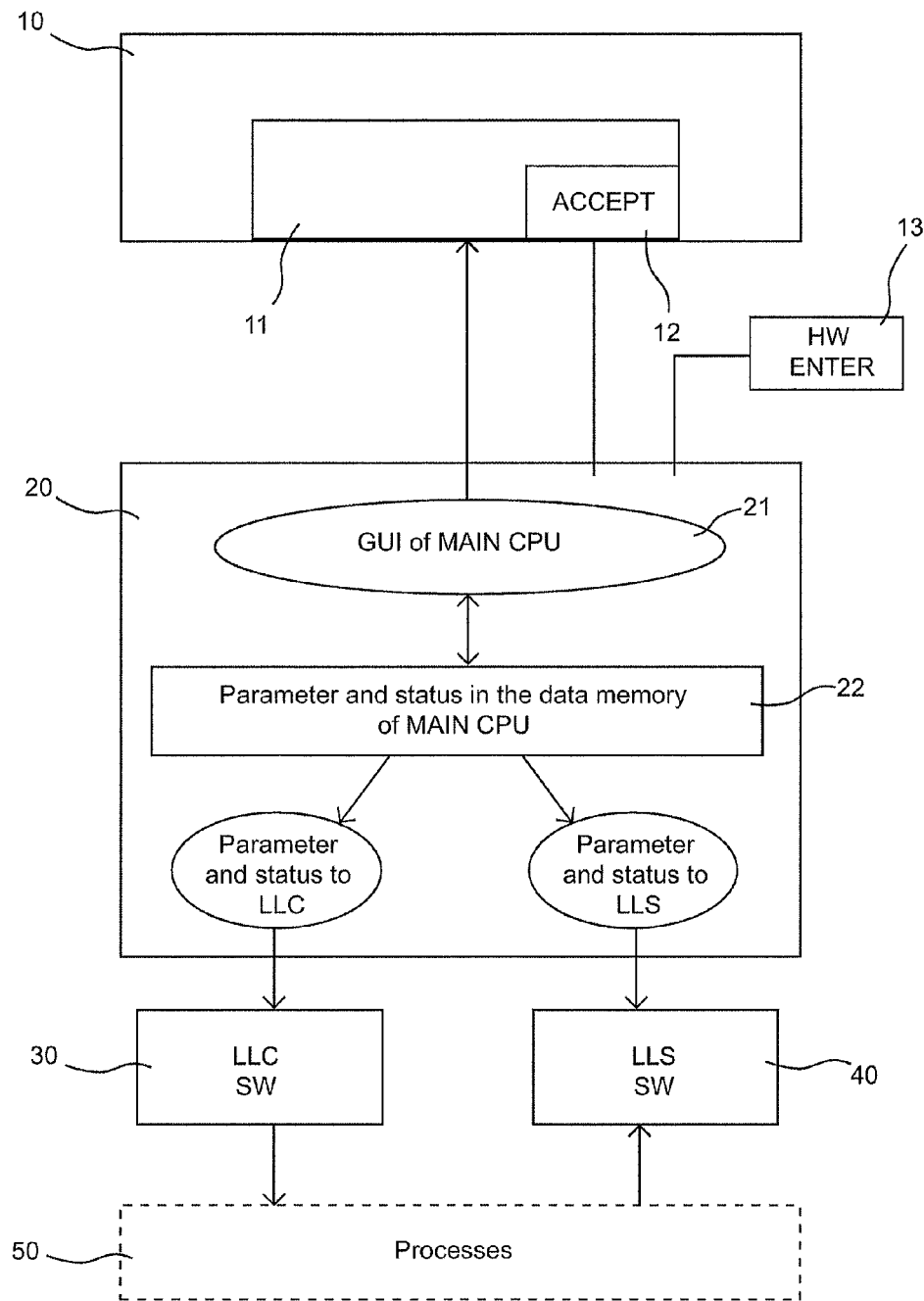
FIG. 1 an example of a system architecture to implement the method according to aspects of the invention.

FIG. 1 shows a diagram depicting the basic features of a system architecture of a microprocessor controlled extracorporeal blood treatment device (ECB device), which is one example of a medical apparatus for which the invention can be used. The ECB device comprises at least an extracorporeal blood circuit, pumps and sensors (not shown) and a software component 20 that controls processes 50 for performing the therapy functions of the ECB device. The ECB device also comprises a screen 10 on which a batch parameter setting input window 11 can be displayed by the general user interface (GUI) of the software component 20 that runs on the main CPU of the ECB device. Preferably, the screen 10 is a touchscreen which allows display and input of information by a user of the ECB device.

According to aspects of the embodiment of FIG. 1, the software component 20 provides parameter settings and statuses to two software units 30 and 40. The first software unit 30 is a control unit (LLC) that controls the processes 50 of the device based on these parameter settings and statuses. The same parameter settings and statuses are provided to a supervisor unit (LLS) 40 that also receives data from the processes 50 and monitors these processes based on the received data and the parameter settings/statuses. Thereby, a safety relevant input procedure can ensure that the parameters settings and statuses which are used by the control unit 30 and the supervisor unit 40, are the same.

The software component 20 drives a user interface 21 that is connected to the screen 10 and comprises means for displaying the batch parameter input window 11 on the screen 10. When parameters have been input in this input window 11 by an operator, they can be confirmed by touching a software accept button 12, for example. Alternatively or in addition, a hardware enter button 13 can be provided which can be pressed to confirm an amended parameter setting.

Upon confirmation, the software component 20 stores the parameter settings and their status in the local memory of the input window 11 and in the data memory 22 of the main CPU, respectively. The corresponding input window 11 can be closed, and the processes 50 of the ECB device are controlled by the control unit 30 based on the amended/new parameter settings. If amended parameters are not confirmed within a certain time period, they can be cancelled and the current settings remain unchanged.

The operation procedure always starts with the opening of the corresponding input window 11. Then, a current set of mutually dependent parameters (batch) is displayed in the input window 11, and preferably any of the parameters can be adjusted. At the same time, ranges of possible values are determined and displayed for each parameter to indicate to the user within which range a parameter can be changed. The adjustment of parameters within these ranges can then be performed manually by a user, automatically or by the time passed during therapy. Selecting any of such parameters is inherently done by adjusting it, or the corresponding parameter has to be selected in order to be adjustable. Thus, the step of selecting a parameter is not necessary if any of them may be changed separately and directly. Preferably, a parameter cannot be modified to values below or above its range values, but one has to keep in mind that these range values can change as a function of other parameters and/or time passed during the therapy.

If the modification of a value leads to an amendment of one or more dependent parameters, this adjustment is automatically performed and displayed in the input window. Thereby, rules of relationships between the parameters are used. These rules of relationship can be stored in the data memory 22 of the main CPU, and may affect the range values, too. However, if by this adjustment a dependent parameter reaches one of its limits, the dependent parameter is not changed beyond this limit. This means that the parameter which is to be modified by the user cannot be modified to certain values in order to comply with the range values of the dependent parameter. Therefore, the possible values of a parameter can be restricted directly by its range values, and indirectly by the range values of dependent parameters. Alternatively, if parameters can be changed beyond their range values, the operator should be informed of this condition by any kind of alarm, for example.

The batch parameter input window 11 can be implemented in different ways, whereby the chosen implementation and design can be adopted to the design of other windows of the application, for example. In one embodiment of the invention, the user can choose and even switch between different designs.

Figure 2:
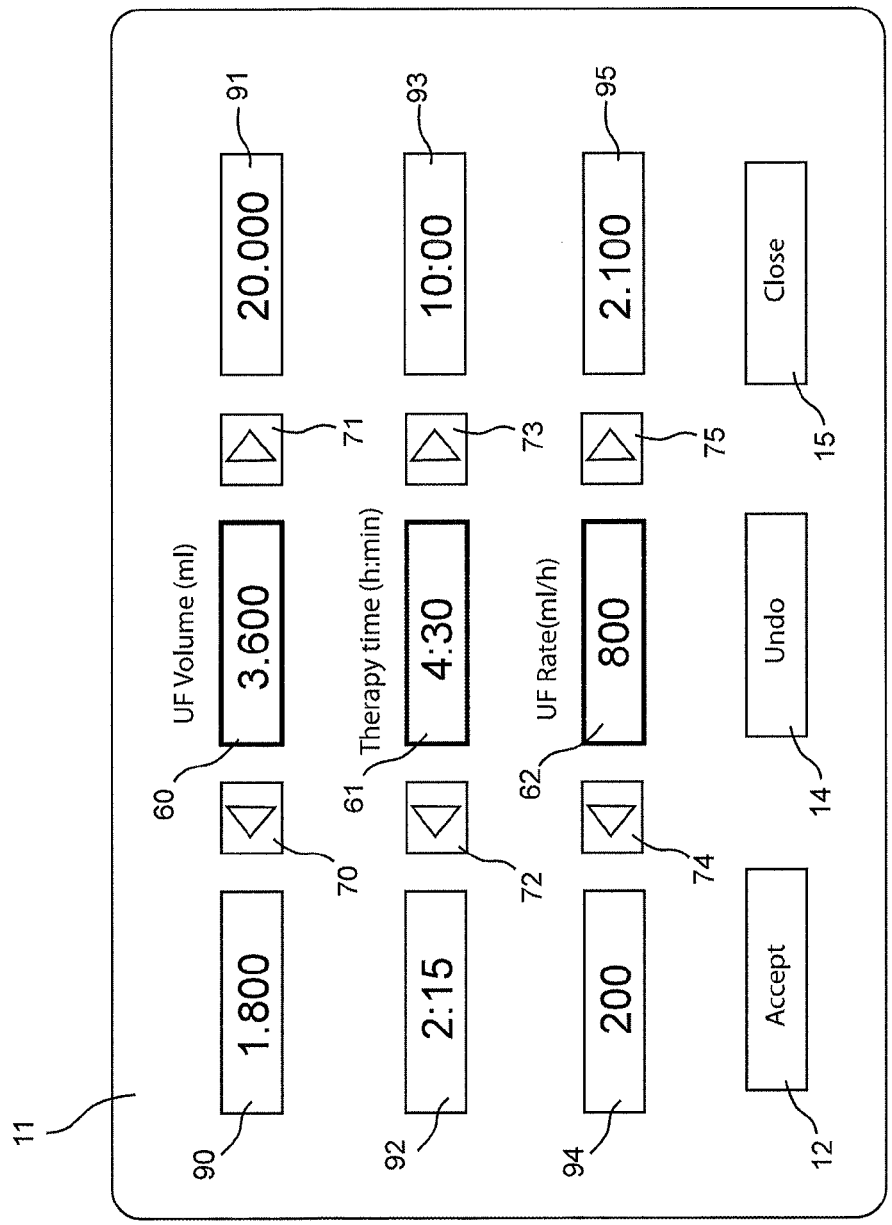
FIG. 2 a numerical input window for parameter input according to a first embodiment of the invention.

In a first embodiment of the invention, the batch parameter input window 11 is implemented in numerical form. A possible embodiment of such numerical input window 11 is shown in FIG. 2. Thereby, current parameters like the ultrafiltration volume (UF volume), the therapy time and the ultrafiltration rate (UF rate) are displayed in numerical parameter fields 60, 61 and 62. Upward/downward buttons 70, 71, 72, 73, 74 and 75 are provided on left and right sides of each parameter field, and these upward/downward buttons can be used to increase or decrease the value of the corresponding parameter setting. For example, each left button 70, 72, 74 can be used to decrease a value, whereas each right button 71, 73, 75 can be used to increase the corresponding value.

In another alternative, only two upward and downward buttons are provided which can be used to set all parameters 60, 61 and 62. Then, means have to be provided to select a parameter that is to be modified by the upward/downward buttons.

Next to the upward/downward buttons, further numerical range fields 90, 91, 92, 93, 94 and 95 are arranged that indicate possible values for each parameter. Thereby, the lowest possible value is displayed left of each input field 60, 61, 62 in range fields 90, 92 and 94, whereas the highest possible value is displayed right of each input field 60, 61, 62 in range fields 91, 93, and 95. From these range fields the operator can see within which range the corresponding parameter can be set. Some of these range values can be fixed, but at least some of them are variable as they depend on other parameters and/or the time passed during the therapy.

The variable range values are automatically set, and the UF rate of biologic algorithm is an example for such automatically set parameter. Furthermore, the lowest limit for the UF volume is equal to the actual UF volume at the current therapy time. The same applies to the lowest limit for the therapy time which is equal to the actual therapy time, where the actual therapy time is the real time passed except for the periods of bypass status of dialyzing fluid. These lowest values of the UF volume and the therapy time are automatically adjusted, too. Another example for an automatically set parameter is the HDF-Bag Infusion volume considering the infusion boluses administered from the same set of bags.

If an operator now wishes to change the ultrafiltration volume manually, he/she pushes the upward/downward buttons 70 or 71 accordingly. Then, the value displayed in the input field 60 changes. The value can be changed stepless, or each push on a button can change the ultrafiltration volume in steps of several milliliters to simplify the input, whereby constant pressure on the button changes the value continuously. In one embodiment of the invention, the operator can choose the size of these steps in a setup menu.

Thereby, the operator can see from the range fields 90 and 91 within which range the ultrafiltration volume can be changed. The operator will not change the UF volume inappropriately, and usually no alarm is needed to avoid false inputs. The minimum value in the range field 90 will automatically change during therapy, whereas the maximum value in the range field 91 can remain constant. Therefore, the operator can set a very high UF volume, but cannot set a UF volume below the low limit in field 90. If the user tries to further decrease the parameter setting in the input field 60 by pushing the downward button 70, this will not be possible.

When the operator changes a parameter, rules for relationships between mutually dependent parameters are applied, and if the change of one parameter affects other parameters, these dependent parameters are changed based on these rules. This change of dependent parameters is immediately determined and displayed in the respective input fields, too. Hereby, the user can see how his/her amendment influences other parameter settings. If the ultrafiltration volume is increased, for example, this has an effect on the therapy time, and the operator can see this dependency when he/she manually changes the ultrafiltration volume. Furthermore, the operator can also see from the range fields 92 and 93 for the therapy time, within which range the therapy time as dependent parameter can be changed. Thus, if the user tries to change the ultrafiltration volume within its possible range limits, he/she can see that this change is also limited by the possible range values for dependent parameters like the therapy time. The same applies vice versa, and reduces the need for explanatory messages why a parameter value had to be refused.

If the batch parameter setting is finished by the operator, a soft button 12 can be pressed to confirm the amended values. The values can also be undone by pressing an "Undo"-button 14. If the user wishes to change to another window or menu, the "Close"-button 15 can be pressed. Alternatively or in addition, buttons with one or all of these functions can be implemented as hardware buttons.

Figure 3:
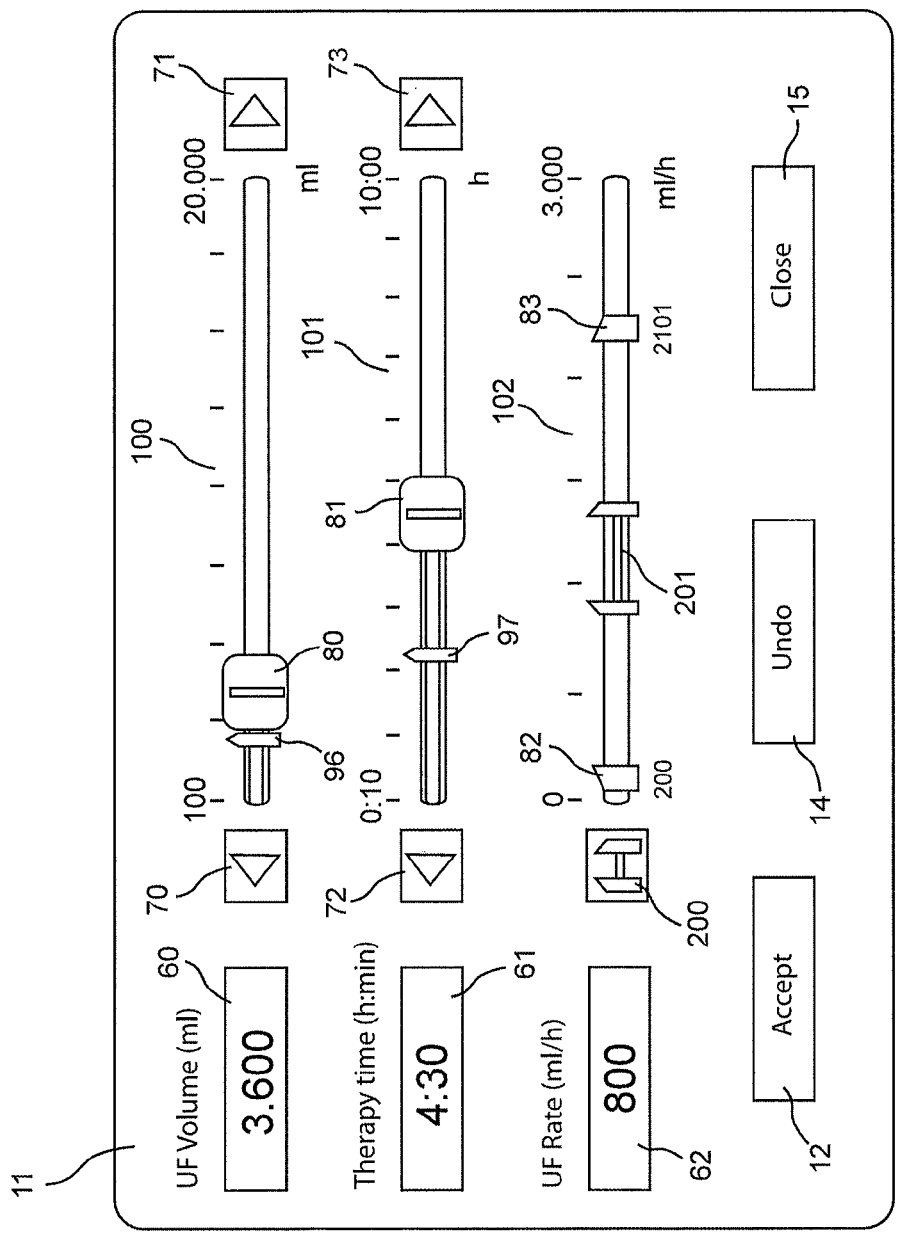
FIG. 3 a slider pad for parameter input according to a second embodiment of the invention.

In a second embodiment of the invention, the batch parameter input window 11 is implemented by a slider pad which is shown in FIG. 3. Parameters like the UF volume, the therapy time and the UF rate can be set again, and the current value of each parameter is displayed in numerical form in input fields 60, 61 and 62. Furthermore, the input parameters are graphically represented by several sliders that can be moved along corresponding scales 100, 101 and 102. These sliders 80, 81, 82 and 83 can manually be moved by dragging a slider along each scale of possible values of equipment specification. If a manual slider 80, 81, 82, 83 is moved, the numerical representation in the respective fields 60, 61 and 62 changes accordingly. Thus, the position of sliders represents the value of an input parameter, which is echoed/displayed in numerical form, too.

In addition, the scales for the UF volume and the therapy time can have upward/downward buttons 70, 71, 72 and 73 on each side. The corresponding parameter can also be increased or decreased by pressing these buttons, whereby the corresponding manual sliders 80, 81, 82, 83 are adjusted accordingly. Preferably, the input value can be decreased by pressing a left button 70 or 72, and can be increased by pressing a right button 71 or 73. The modification can again be stepless, or each push on a button can change the respective value in steps of several units to simplify the input.

Furthermore, if another parameter is affected by the change of a parameter, this dependent parameter is automatically adjusted by movement of the corresponding manual slider and the respective numerical indication. Thereby, stored rules for relationships between the parameter settings are used. For example, if manual slider 81 is moved along axis 101 to adjust the therapy time, manual slider 80 is automatically moved along axis 100 to adapt the ultrafiltration volume, too.

To indicate to the operator within which range a parameter can be adjusted, fixed values on the scales 100, 101 and 102 are used in combination with variable range values that are indicated by automatically set sliders 96 and 97. The position of the automatically set sliders 96, 97 is again determined based on the time passed during the therapy and/or other parameter settings. Thus, the position of the automatically set sliders 96 and 97 can change at least as a function of the therapy time and/or the adjustment of parameter settings again. This means that the scales of sliders might be further limited/restricted by upper and lower limiters, which are either input sliders themselves, or just automatic devices representing any kind of other limitations of any sources for the given input parameter.

For example, automatically set slider 97 for the minimum therapy time will automatically move to the right when therapy time passes by. This shows the operator that the therapy time can be adjusted between this lowest value and a fixed maximum value of 10 hours, for example. At the same time, the passed therapy time influences the position of automatically set slider 96 which indicates the minimum ultrafiltration volume. Thus, the operator will not try to change a parameter below or above these values and no alarm should be needed to avoid inappropriate parameter settings.

However, any input limitation might also be changed in any scale depending on priority decisions about the order of parameter setting. This can even occur in the derived scale by proper signaling the potentially unsafe situation. For example, if the UF volume is increased, the therapy time can be increased automatically, if the UF rate's upper limit was reached. Alternatively, if the therapy time is considered more important than the upper limit of the UF rate, the upper limit of the UF rate may be increased automatically. This can be accompanied by changing its color to yellow or red, until the end of the scale of the equipment specification of UF Rate would be reached.

The derived parameter might be not just a single value, but a range, too. In such embodiment, the range depends on a set of input data, which is set in another input window. Then the above described limitation of the derived parameter is meant for the whole range, i.e. all values of the range of the derived parameter. The allowable input parameter range is then defined by the upper/lower limiters of its scale or by the upper/lower limiters of the derived parameter scale, whatsoever is stricter, i.e. gives smaller value for the upper limit or bigger value for the lower limit of the input parameter. The dragging of a slider is then allowed within the allowable range of upper and lower limits only, regardless of whether they are defined by its scale or the derived parameter scale.

For example, a special axis with profile input can be provided for the ultrafiltration rate. When a corresponding profile button 200 is pressed, a window for a profile setting can open, whereby this kind of profile setting is known. It offers the option to choose stored UF-profiles or create a new UF-profile. The desired ultrafiltration rate can be input, whereby there must be a scale of percentage values around 100% which is the average UF rate. The integrated value of UF rate profile must be equal to the set UF volume. The minimum and maximum values in this profile, or a profile set by any different way, will then determine the range of derived parameters indicated by a range 201 on scale 102. From this profile range 201, the operator can see that the maximum value for the manual slider 82 is limited by the left side of the profile range 201, and the minimum value for the manual slider 83 is limited by the right side of the profile range 201. Thereby, the width of the profile range 201 can change.

In one embodiment of the invention, the system stops dragging sliders and reacts by audio/voice feed-back and/or other visual feed-back, when a limiter is reached or touched. If a manual slider 80, 81, 83, 84 is even left at a limiter, the position of which depends on something else than another input value (depends primarily on time), then the slider might by pushed/adjusted automatically (without user dragging) by the non-input driven limiter, however, giving proper audio/voice and/or visual feed-back from the operation.

Preferably, the slider pad 11 provides for the same hardware buttons or soft buttons 12, 14 and 15 to confirm or undo values, and to close the input window 11. Furthermore, beyond the slider pad operations there can be other parameter setting ways. For example, a calculator pad can open when a displayed value is pressed.

For all embodiments of batch parameter input windows 11 different confirmation scenarios can be implemented. For example, no confirmation window is used at all, or there is a confirmation window, but without safety relevant checking. In a third case, there is a confirmation window of safety relevant check. However, the differences of the cases and the condition of validating/confirming the values of parameters are not relevant from the operation procedure point of view. The need of confirmation windows and/or confirmation window of safety relevant check at parameter input is the subject of design decisions based upon the risk management of the system.

The invention claimed is:

1. A microprocessor controlled medical apparatus for setting parameters, said medical apparatus comprising, a user interface for setting an adjustable parameter and at least one dependent parameter;

a screen for displaying the adjustable parameter and the at least one dependent parameter;

a storage unit in which a set of rules is stored, the set of rules defining relationships between the adjustable parameter and the at least one dependent parameter;

wherein in real time and upon a change of the adjustable parameter, a range of the at least one dependent parameter, including an upper limit of the range and a lower limit of the range, is determined as a function of the set of rules defining relationships between the adjustable parameter and the at least one dependent parameter;

wherein the range of the at least one dependent parameter, including the upper limit and lower limit of the range, is automatically determined and adjusted during a therapy using the medical apparatus and wherein the automatic determination and adjustment occur as a function of a therapy time; and wherein the determined upper limit of the range and the determined lower limit of the range is displayed on the screen in real time and as the adjustable parameter is changed.

2. The microprocessor controlled medical apparatus according to claim 1, wherein a value of the adjustable parameter, the range of the at least one dependent parameter, or a combination thereof, for the adjustable parameter, the at least one dependent parameter, or both, is displayed in numerical form.

3. The microprocessor controlled medical apparatus according to claim 1, wherein the adjustable parameter, the at least one dependent parameter, the range of the at least one dependent parameter, or a combination thereof, are displayed by sliders on a labeled scale.

4. The medical apparatus of claim 1, wherein the at least one dependent parameter includes a first dependent parameter and a second dependent parameter, and wherein in real time and upon the adjustment in the adjustable parameter, a range of the first dependent parameter and a range of the second dependent parameter, including upper limits and lower limits for each range, are determined as a function of the set of rules.

5. A method for setting parameters of a microprocessor controlled apparatus, the method comprising the steps of:
displaying on a screen an adjustable parameter and at least one dependent parameter;
adjusting, via a user interface, the adjustable parameter upon manual selection by an operator;
determining, in real time and upon adjustment of the adjustable parameter, a range of the at least one dependent parameter, including an upper limit of the range and a lower limit of the range, as a function of a set of rules defining relationships between the adjustable parameter and the at least one dependent parameter;
wherein the range of the at least one dependent parameter, including the upper limit and lower limit of the range, is automatically determined and adjusted during a therapy using the medical apparatus and wherein the automatic determination and adjustment occur as a function of a therapy time; and
displaying the determined upper limit of the range and the determined lower limit of the range of the at least one dependent parameter on the screen in real time and as the adjustable parameter is adjusted.

6. Method according to claim 5, wherein the dependent parameter cannot be adjusted to values beyond the determined upper limit of the range and the determined lower limit of the range of the dependent parameter.

7. Method according to claim 5, wherein the dependent parameter can be adjusted to values beyond the determined upper limit of the range and the determined lower limit of the range of the dependent parameter, and an adjustment beyond the determined upper limit of the range or the determined lower limit of the range of the dependent parameter is indicated visually, acoustically, or by a combination thereof.

8. Method according to claim 5, wherein the determination of the at least one dependent parameter, the determined range, or a combination thereof, is based on additional data that is provided to the software.

9. Method according to claim 5, wherein the determination of the at least one dependent parameter, the determined range, or a combination thereof, is based on priority rules that are stored in a storage unit.

10. Method according to claim 5, wherein the adjustable parameter is adjusted to possible values, when a mutable limiter of the time dependent range of possible values becomes equal to a current parameter.

11. Method according to claim 5, wherein it is indicated visually, acoustically, or a combination thereof, when a mutable limiter of the time dependent range of possible values becomes equal to a current parameter.

12. Method according to claim 5, wherein the screen is a touchscreen, and a batch setting acceptance operation for implementing a set of amended parameters is actuated by a soft button on the touchscreen.

13. Method according to claim 5, wherein a batch setting acceptance operation for implementing a set of amended parameters is actuated by a hardware button at a extracorporeal blood treatment device.

14. Medical apparatus, comprising a software component driving a user interface connected to a screen and a storage unit in which a set of rules is stored that defines the relationship between an adjustable parameter and at least one dependant based on which the medical apparatus is operated, wherein the medical apparatus is configured for manual selection of the adjustable parameter and the at least one dependant parameter by an operator and for setting and implementing the adjustable parameter and the at least one dependent parameter with the method according to claim 5.

15. Medical apparatus according to claim 14, wherein the medical apparatus is an extracorporeal blood treatment device.

16. The method of claim 5, wherein the at least one dependent parameter includes a first dependent parameter and a second dependent parameter, and wherein in real time and upon the adjustment in the adjustable parameter, a range of the first dependent parameter and a range of the second dependent parameter, including upper limits and lower limits for each range, are determined as a function of the set of rules.

17. A microprocessor controlled medical apparatus for setting parameters, said medical apparatus comprising:
a user interface for setting an adjustable parameter, wherein the adjustable parameter is associated with at least two dependent parameters, each dependent parameter having a range including an upper limit and a lower limit;
a screen for displaying the adjustable parameter and the at least two dependent parameters;
a storage unit in which a set of rules is stored, the set of rules defining relationships between the adjustable parameter and the at least two dependent parameters;
wherein, in real time and upon the adjustment of the adjustable parameter, a first range of a first of the at least two dependent parameters and a second range of a second of the at least two dependent parameters, including upper limits and lower limits for each range, are determined as a function of the set of rules; wherein at least one of the range of the first dependent parameter or the range of the second dependent parameter, including the upper limit and lower limit of the range, is automatically determined and adjusted during a therapy using the medical apparatus; wherein the automatic determination and adjustment occur as a function of a therapy time; and wherein the determined upper and lower limits of each of the determined ranges is displayed on the screen in real time and as the adjustable parameter is changed.

* * * * *